US00PP07776P

United States Patent [19]

Fischer

[11] Patent Number: Plant 7,776

[45] Date of Patent: Jan. 28, 1992

[54] AFRICAN VIOLET PLANT NAMED ANNIFI

[76] Inventor: Arnold Fischer, Kahlendamm 22, 3000 Hannover 51, Fed. Rep. of Germany

[21] Appl. No.: 524,068

[22] Filed: May 16, 1990

[51] Int. Cl.[5] ..... A01H 5/00
[52] U.S. Cl. ..... Plt./69
[58] Field of Search ..... Plt./69

[56] References Cited

U.S. PATENT DOCUMENTS

P.P. 6,575 1/1989 Holtkamp ..... Plt./69

*Primary Examiner*—James R. Feyrer
*Attorney, Agent, or Firm*—Burns, Doane, Swecker & Mathis

[57] ABSTRACT

A new and distinct cultivar of African violet named Annifi is provided. This cultivar exhibits a compact miniature growth habit, light green pubescent foliage, and forms in abundance on upright peduncles attractive white single zygomorphic rotate flowers having substantially no petal undulation. The plant advantageously has a very floriferous habit with the flowering continuing for many weeks following its onset.

2 Drawing Sheets

SUMMARY OF THE INVENTION

The present invention comprises a new and distinct cultivar of African violet plant, botanically known as *Saintpaulia ionantha*, and hereinafter referred to by the cultivar name Annifi.

The new cultivar is the product of a planned breeding program and was referred to during the breeding and selection process by the designation 087-226-003. The basic objective of the breeding program was to create a new miniature highly floriferous and compact African violet cultivar having an abundance of single white flowers which stand erect above light green foliage.

The new cultivar originated from a cross made in this breeding program at Hannover, West Germany. The female and male parents are unknown at this time. The discovery and selection of the new cultivar occurred during 1987.

Asexual reproduction of the new cultivar by leaf cuttings, as performed by me at Hannover, West Germany and at Fallbrook, Calif., U.S.A. has demonstrated that the combination of characteristics as herein disclosed for the new cultivar are firmly fixed and are retained through successive generations of asexual propagation.

Annifi has not been observed under all possible environmental conditions to date. Accordingly, the phenotype may vary significantly with variations in the environment, such as temperature, light intensity, day length, etc.

The observations, measurements, and values expressed herein describe the new cultivar when grown under greenhouse conditions at Hannover, West Germany. These conditions are believed to closely approximate those commonly used in commercial practice.

The following traits have been repeatedly observed and are believed to be the basic characteristics of Annifi which in combination distinguish it as being a new and distinct African violet cultivar:

(a) forms attractive white single zygomorphic rotate flowers having substantially no undulation of the petals, (b) forms light green pubescent foliage comprising oval leaves with a slightly creanate margin having a narrow apex and a cordate base,
(c) exhibits a compact miniature rosette growth habit with the flowers being held erect above the foliage on upright peduncles, and
(d) exhibits a very floriferous habit with the flowers continuing to open for many weeks after the onset of flowering.

The flowers commonly exhibit a diameter of approximately 2.5 cm. When started as 6 to 8 leaf-stage plantlets, Annifi commonly finishes in 8 to 10 weeks when grown in 5 to 6 cm. pots depending upon the growing conditions encountered.

Since the new cultivar is considered to be unique, it is not meaningful to compare its characteristics to those of any previously known African violet variety.

BRIEF DESCRIPTION OF THE PHOTOGRAPHS

The accompanying photographs show as nearly true as it is reasonably possible to make the same, in color illustrations of this character, typical specimens of the plant and flowers of the new cultivar. The plants of the new variety were grown in a greenhouse at Hannover, West Germany.

FIG. 1 illustrates a typical specimen of the overall plant of the new cultivar wherein the compact miniature growth habit, foliage and blossoms are shown, and FIG. 2 illustrates from above at the right four typical flowers of the new cultivar, and at the left a portion of a page from the R.H.S. Colour Chart of The Royal Horticultural Society, London, for comparative purposes.

DETAILED DESCRIPTION

Figure 1:
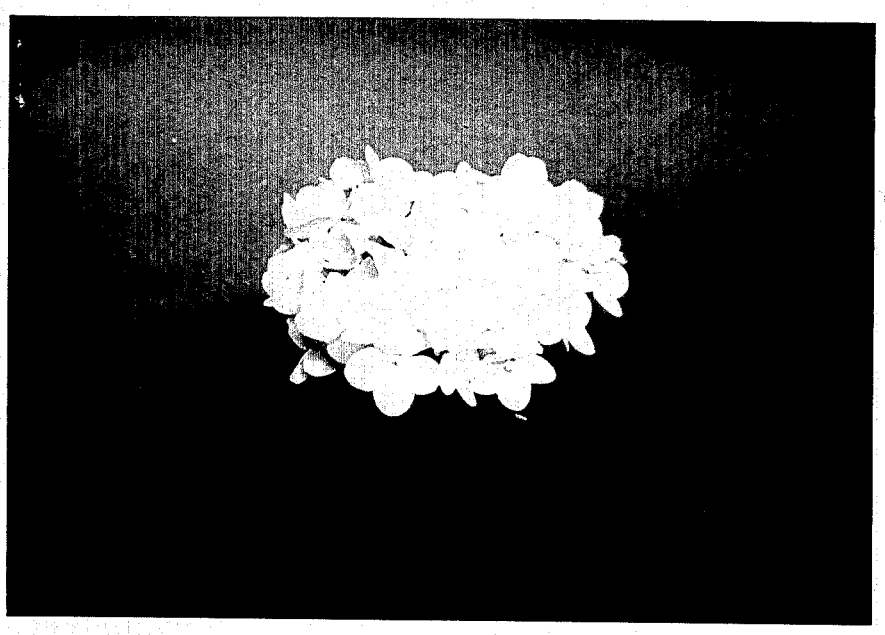
Figure 2:
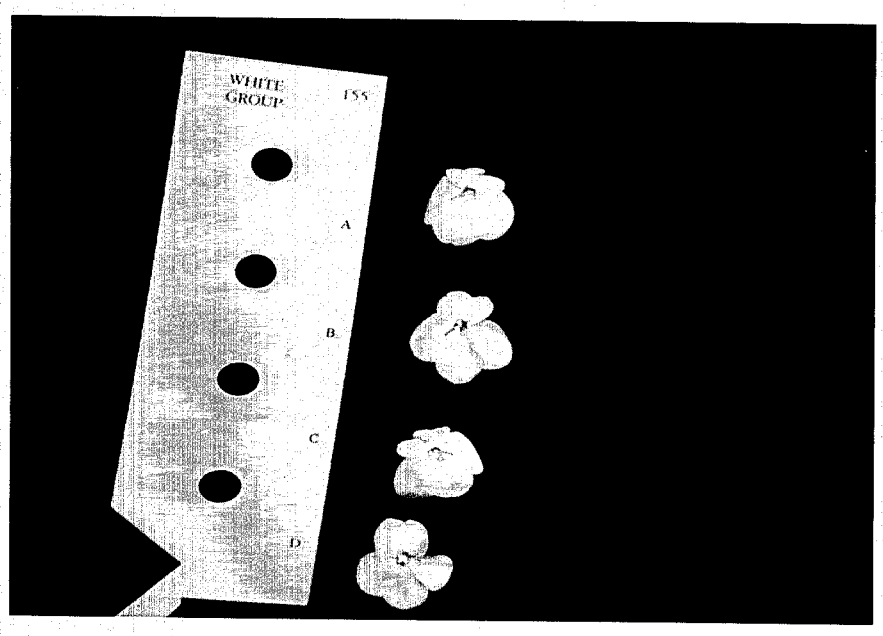

The chart used in the identification of the colors described hereafter is that of The Royal Horticultural Society (R.H.S. Colour Chart) except where general color terms of ordinary dictionary significance are expressed. The color values were taken under natural daylight conditions at 11 a.m. at Hannover, West Germany.

Botanical classification: *Saintpaulia ionantha,* Ramat., cv. Annifi

Parentage: Unknown.

Propagation: The new cultivar holds its distinguishing characteristics through successive propagations by leaf cuttings.

Plant: Commonly from approximately 4 to 5 cm. tall when grown in pots, and approximately 9 cm. in diameter when fully grown. The growth rate of plant is vigorous and the general shape of the fully grown plant is miniature, compact and rosette.

*Leaves.*—Quantity: Abundant. Shape: Oval shaped with a slightly crenate margin, having a narrow apex and a cordate base. Size: Approximately 2.5 cm. in length on average×approximately 2.5 cm. in width on average. Texture: Pubsecent and glossy. Ribs and veins: Pinnate. Color — upper surface: Green Group 137C. Color — under surface: Yellow-Green Group 147D. Petioles: Yellow-Green Group 147D.

*Flowers.*—Buds: Size: Approximately 0.5 to 0.7 cm. in diameter on average. Shape: Round. Rate of opening: Normal. Sepals: Shape: 5 in number, lanceolate. Color: Green Group 137 C. Phyllaries: Shape: 2 in number, lanceolate. Color: Light green. Calyx: Size: Approximately 0.3 cm. in diameter on average. Shape: Funnel-shaped. Aspect: Pubescent. Peduncle: Length: Approximately 3 to 4 cm. om average. Character: Erect, rigid. Color: Yellow-Green Group 144D.

*Individual flowers.*—Number of petals: 5. Size: A diameter of approximately 2.5 cm. and a depth of approximately 1 cm. commonly are exhibited. Shape: Single zygomorphic rotate; and in the shape of a cup as the bloom first opens and changing to a somewhat flat configuration with maturity. Color — upper surface: White Group 155D. Color — under surface: White Group 155D. The flower coloration can vary somewhat due to the amount of light, fertilizer, temperature and other growing conditions. Bearing: Cymose clusters on upright peduncles. Flowering Habit: Flowers profusely and intermittently throughout the year with blooms commonly lasting approximately 3 to 4 weeks after which petals dry up but do not drop; finishes in approximately 8 to 10 weeks when a 6 to 8 leaf-stage plantlet is grown in a 5 to 6 cm. pot.

*Reproductive organs.*—Stamens: Borne singly on one side of the ovary; 2 anthers are basifixed. Anthers: 2 in number; monodelphous arrangement; approximately 0.2×0.2 cm.; yellow. Filaments: approximately 0.3 cm.; Yellowish-white. Pollen color: Yellow. Pistils: Number: 1 in number. Styles: Approximately 0.5 to 0.7 cm. in length, violet. Stigma: Sticky, white. Ovaries: Hypogynous and tomentose.

Disease resistance: No African violet diseases have been observed to date.

I claim:

1. A new and distinct cultivar of African violet plant named Annifi characterized by the following combination of characteristics:

(a) forms attractive white single zygomorphic rotate flowers having substantially no undulation of the petals, (b) forms light green pubescent foliage comprising oval leaves with a slightly crenate margin having a narrow apex and a cordate base, (c) exhibits a compact miniature rosette growth habit with the flowers being held erect above the foliage on upright peduncles, and (d) exhibits a very floriferous habit with the flowers continuing to open for many weeks after the onset of flowering:

substantially as herein shown and described.

* * * * *